(12) United States Patent
Otto et al.

(10) Patent No.: US 7,973,006 B2
(45) Date of Patent: Jul. 5, 2011

(54) ANTIBACTERIAL AGENT BASED ON FATTY ACID ESTERS OF HYDROXY CARBOXYLIC ACID ACIDS

(75) Inventors: Roel Otto, Gorinchem (NL); Aldana Mariel Ramirez, Wageningen (NL); Diderik Reinder Kremer, Groningen (NL)

(73) Assignee: Purac Biochem B.V., Gorinchem (NL)

( * ) Notice: Subject to any disclaimer, the term of this patent is extended or adjusted under 35 U.S.C. 154(b) by 48 days.

(21) Appl. No.: 12/232,424

(22) Filed: Sep. 17, 2008

(65) Prior Publication Data
US 2009/0082253 A1    Mar. 26, 2009

Related U.S. Application Data

(60) Provisional application No. 60/960,131, filed on Sep. 17, 2007.

(51) Int. Cl.
*A61K 38/00* (2006.01)
*A61K 31/225* (2006.01)
*A01N 37/02* (2006.01)
*A01N 37/06* (2006.01)

(52) U.S. Cl. .................................. 514/1.1; 514/547

(58) Field of Classification Search .................. None
See application file for complete search history.

(56) References Cited

U.S. PATENT DOCUMENTS

| 3,275,503 | A |   | 9/1966 | Marnett et al. |
| 5,494,937 | A | * | 2/1996 | Asgharian et al. ......... 514/772.3 |

FOREIGN PATENT DOCUMENTS

| EP | 0 572 271 B1 | 1/1997 |
| EP | 1 000 542 B1 | 6/2002 |
| JP | A-04-008273 | 1/1992 |
| JP | A-05-068521 | 3/1993 |
| JP | A-07-135943 | 5/1995 |
| JP | A-2000-026887 | 1/2000 |
| JP | A-2000-270821 | 10/2000 |

OTHER PUBLICATIONS

Shima et al., "Antimicrobial Action of $\epsilon$-Poly-$_L$-Lysine", *The Journal of Antibiotics*, vol. XXXVII No. 11, Jan. 19, 1984, pp. 1449-1455.
Hiraki et al., "Report of Research & Development $\epsilon$-polylysine: its Development and Utilization", *Fine Chemicals*, vol. 29, 2000, pp. 18-25.

* cited by examiner

*Primary Examiner* — Marcela M Cordero Garcia
(74) *Attorney, Agent, or Firm* — Oliff & Berridge, PLC (57) ABSTRACT

The present invention relates to an antibacterial composition based on a combination of fatty acid ester of fatty acid and hydroxy carboxylic acid with an antibacterial agent selected from polylysine, protamine, their salts and mixtures hereof. The hydroxy carboxylic acid may be present as acid in its free form, in its salt form and/or in its ester form.

The present invention further is directed to the use of said composition as antibacterial agent against gram-negative bacteria in various products, applications and methods. Furthermore, the present invention is related to products comprising said antibacterial agent.

10 Claims, 8 Drawing Sheets

ANTIBACTERIAL AGENT BASED ON FATTY ACID ESTERS OF HYDROXY CARBOXYLIC ACID ACIDS

This nonprovisional application claims the benefit of U.S. Provisional Application No. 60/960,131, filed Sep. 17, 2007.

The present invention relates to an antibacterial composition based on fatty acid ester of hydroxy carboxylic acid and to its use as antibacterial agent against gram-negative bacteria in various products and applications. The present invention further relates to products and in particular to food products comprising said antibacterial agent.

The fatty acid esters of the present invention comprise fatty acid ester of hydroxy carboxylic acid such as for example lactic acid, citric acid, malic acid, gluconic acid and tartaric acid wherein said hydroxy carboxylic acid can also be in a salt- or ester form. Further, the hydroxy carboxylic acid may comprise one or more polymerized acid monomers, such as is the case in for example lactylates.

The majority of these fatty acid esters of hydroxy carboxylic acids are applied as emulsifier. For example, fatty acid esters of lactic acid, also referred to as lactylates and acyl lactylates, are well-known for their emulsifying effect. They are commonly applied in the bakery industry.

Some of the lactylates of interest are described in U.S. Pat. No. 3,275,503, EP 0572271 and EP 1000542 and are represented with the general formula:

wherein RCO is an acyl radical of a fatty acid with 4 to 12 carbon atoms, Y is a cation selected from hydrogen, alkali metal, alkaline earth metal, zinc, silver, ammonium or substituted ammonium having one or more C1-C3 alkyl or hydroxy alkyl groups; n represents the value of the cation and m is an integer of from 1 to n, x is a number of from 1 to 6 and preferably 1 to 3.

The lactylates described in U.S. Pat. No. 3,275,503 have an acyl group RCO with 8 to 12 carbon atoms and are described to inhibit the growth of mildew and mold development by yeasts and fungi originating from e.g. *Rhizopus, Penicillum, Aspergillus, Trichophyton*, and *Saccaromyces*. The lactylates in question also show some antibacterial activity against *Staphylococcus aureus* and *Bacillus mesentericus*, which are both gram-positive bacteria.

The lactylates described in EP 0572271 have an acyl group RCO with 4 to 7 carbon atoms and have some antibacterial activity against *Pseudomonas cepacia*, which is a gram-negative bacterium.

EP 1000542 describes the sodium salt of capryl-lactyl-lactylate having some antimicrobial activity against *Enterococcus faecalis*, which is a gram-positive bacterium, and against *Candida albicans*, which is a fungus.

Lactylates, and more in particular lactylates of the above formula having an acyl group RCO with 8 to 12 carbon atoms, are however not known to be very effective against gram-negative bacteria such as e.g. *Escherichia coli, Salmonella* and *Campylobacter*. They are therefore also not used as antibacterial agents. In fact, their regulatory status is that of them being used as emulsifying agent only.

The same applies to fatty acid esters of other hydroxy carboxylic acids such as for example the fatty acid esters of citric acid, malic acid and tartaric acid. These esters are mainly used as emulsifiers in various types of products and not for antibacterial purposes.

The present invention provides a solution to overcome above-mentioned lack in efficiency against gram-negative bacteria. The present invention provides a means to render the group of fatty acid esters of hydroxy carboxylic acids as described above significantly more active against gram-negative bacteria, thereby making them very useful as antibacterial agents for application in a wide variety of food, drink and other products such as e.g. in feed applications, in detergents and cosmetic products.

Hereto, the present invention is directed to an antibacterial composition comprising a combination of fatty acid ester of fatty acid and hydroxy carboxylic acid and/or the salt and/or ester of said hydroxy carboxylic acid with one or more antibacterial agents selected from polylysine, protamine and their salts.

It is found that the above-mentioned antibacterial agents not simply enhance the activity of fatty acid esters of hydroxy carboxylic acids whereby said enhancing effect is the sum of the individual activities of the fatty acid ester and the antibacterial agent, but the antibacterial agent and the fatty acid ester of the present invention work in synergy resulting in an antibacterial activity which is significantly higher than the sum of the activities of the individual components of the antibacterial composition. Due to this synergy the fatty acid ester of the present invention can be very effectively used as antimicrobial agent in a composition comprising polylysine, protamine, their salts or any combination hereof.

Polylysine is known to exert an antibacterial activity against gram-negative bacteria. Both α-polylysine and ε-polylysine have antibacterial activity although the latter one in significant greater extent as described by Shima et al. (Nov. 1984). The article describes that ε-polylysine can effectively be used against gram-positive and -negative bacteria such as for example *Escherichia coli* in concentrations of about 1~8 microgram per ml.

Hiraki et al. (2000) describe combinations of ε-polylysine with antibacterial agents such as glycine, acetic acid/vinegar, ethanol or thiamine laurylsulfonate. No mention is however made of a composition wherein polylysine is combined with fatty acid ester of hydroxy carboxylic acid effective as antibacterial agent against gram-negative bacteria.

JP 2000-270821, JP 7-135943, JP 4-8273 describe compositions comprising ε-polylysine in combination with glycerol fatty acid esters, protamines, ethanol, glycine and/or hydroxy carboxylic acids and their salts. Above-mentioned compositions are described to be effective against yeasts, fungi and putrefactive or food-spoilage bacteria such as *Candida* and *Luconostoc*. The specific combination of polylysine and/or salts hereof with fatty acid ester of hydroxy carboxylic acid is however not disclosed.

Protamine is also a commonly applied antibacterial agent. Many Japanese patent applications describe antibacterial compositions comprising combinations of protamine with various other antibacterial components such as for example glycerides, hydroxy carboxylic acids and/or their salts, amino acids, polylysine, ethanol, etceteras. No mention is made however of the specific combination of protamine and/or salts hereof with fatty acid ester of hydroxy carboxylic acid.

The above-mentioned combinations of fatty acid ester of fatty acid and hydroxy carboxylic acid and/or its salt with polylysine or protamine in their free form and/or in their salt form and/or any combination hereof have thus not been described before. Neither has the synergistic antibacterial activity of said combination against gram-negative bacteria been acknowledged before. The present invention is related to the use of said fatty acid ester of fatty acid and hydroxycarboxylic acid (and/or a salt hereof) as antimicrobial agent in a composition comprising polylysine (and/or a salt hereof), protamine (and/or a salt hereof) or any combination hereof.

The fatty acid ester as used in the antibacterial composition of the present invention is an ester of fatty acid and hydroxy carboxylic acid and/or a salt hereof. As the person skilled in the art knows, such an ester may be obtained via, for example, an esterification or enzymatic process. As is common knowledge, most processes for the manufacture of fatty acid esters result in a mixture of fatty acid esters whereby said mixture is for example a mixture of fatty acid esters of different fatty acid tails or of different ester tails. A specific fatty acid in its pure form may be obtained out of this mixture by various means that are well-known to the person skilled in the art.

The fatty acid reactant may be a saturated or unsaturated fatty acid comprising 4 to 18 and preferably 8 to 18 carbon atoms. Non-limiting examples hereof are butyric acid (i.e. butanoic acid (C4)), caproic acid (i.e. hexanoic (C6)), myristic acid (i.e. tetradecanoic acid (C14)), stearic acid (i.e. octadecanoic acid (C18)), myristoleic acid (C14) and/or oleic acid (C18).

The hydroxy carboxylic acid may comprise one monomer of hydroxy carboxylic acid or several monomers of hydroxy carboxylic acid linked to each other by polymerized bonds. Said monomer of hydroxy carboxylic acid may comprise 1 to 6 carbon atoms such as for example the monomer of lactic acid, malic acid, citric acid, gluconic and tartaric acid. Further, the salts and/or esters of said hydroxy carboxylic acid are also very suitable for the antibacterial composition according to the present invention.

In a preferred embodiment of the present invention, the antibacterial composition comprises fatty acid ester of lactic acid and/or the salt of lactic acid, also referred to as lactylates.

The lactylates of the present invention have the following formula:

wherein RCO is an acyl radical of a fatty acid with 4 to 18 carbon atoms, and preferably 8 to 18 carbon atoms, Y is a cation selected from hydrogen, alkali metal, alkaline earth metal, zinc, iron, ammonium and substituted ammonium having one or more C1-C3 alkyl or hydroxy alkyl groups; n represents the value of the cation and m is an integer of from 1 to n; x represents the number of monomer units and has a value of from 1 to 6 and preferably of from 1 to 3.

Components wherein x is for example 1 are referred to as monolactylates (i.e. comprising only 1 lactic acid molecule) and wherein x is 2 are called dilactylates (comprising 2 polymerized/esterified lactic acid molecules). The lactylate components are often obtained as mixtures of for example a mixture of predominantly monolactylates and further comprising dilactylates due to the way in which they are prepared. It may be very well possible that also higher polymerized lactylates are present in the mixture. The parameters x, m and n as described above thus present average numbers.

The lactylates may be obtained in their pure form (e.g. only the mono-form) by means of for example chromatographic separation or by any other means known to the person skilled in the art.

Good results were obtained with mixtures predominantly containing mono- and/or di-lactylate esters of octanoic acid (C8), or decanoic acid (C10), or dodecanoic acid (C12) or tetradecanoic acid (C14), or palmitic acid (C16), or oleic acid (C18:1) and the sodium, potassium and calcium salts hereof.

The calcium salt of a mono-lactylate ester of e.g. octanoic acid is represented by the above formula wherein RCO is the acyl radical of octanoic acid, x is 1, Y is calcium and thus n representing the value of the cation is 2, and the final parameter m may be 1 (i.e. the calcium hydroxide salt) but is preferably 2.

It has been observed that also esters of lactic acid may be used to form fatty acid esters with, that then may be used in the antibacterial composition of the present invention. Thus, the fatty acid ester of a fatty acid such as for example octanoic acid or dodecanoic acid with a lactate ester such as for example ethyl-lactate works well as antibacterial or antimicrobial agent in combination with one or more antibacterial agents such as polylysine, protamine and/or salts hereof according to the present invention.

Polylysine may be present as ε-polylysine, as α-polylysine or as a mixture hereof. ε-Polylysine is preferred as it has a higher antibacterial activity against gram-negative bacteria than the other forms of polylysine and thus lesser amounts of this antibacterial agent are needed in the applications. ε-Polylysine is a homopolymer containing 25-35 L-lysine residues. The systematic name of ε-polylysine is poly(imino (2-amino-1-oxo-1,6-hexanediyl)). The empirical formula for the typical ε-polylysine homopolymer is $C_{180}H_{362}N_{60}O_{31}$ with a molecular weight of approximately 4700 (30 L-lysine residues). The chemical Abstract Service (CAS) number for ε-polylysine is 28211-04-3. The fatty acid esters of the present invention may also be combined with one or more salts of polylysine. An example hereof is the salt of an inorganic acid such as hydrochloric acid, sulfuric acid, phosphoric acid etceteras or of an organic acid such as lactic acid, acetic acid, propionic acid, fumaric acid, malic acid, citric acid etceteras. Although there is no substantial difference in antibacterial effect, polylysine is sometimes preferably used in the free form because of limited solubility of the polylysine in salt form.

The protamine, a small arginine-rich protein, may also be used in its free form and in the form of a salt. Suitable protamine is for example protamine sulfate or protamine hydrochloride.

Optionally, the antibacterial composition of the present invention may further comprise one or more metal chelating agents. The chelating agent may be selected from for example ethylene diamine tetraacetic acid (EDTA) and salts thereof, diethylenetriaminepenta-acetic acid and salts thereof, various phosphate-based compounds such as sodium hexametaphosphate, sodium acid pyrophosphate and polyphosphoric acid, organophosphonate chelating compounds such as: phytic acid, 1,1-diphosphonic acid, siderophores and iron binding proteins such as enterobacterin and lactoferrin, and hydroxy carboxylic acids and/or salts thereof such as for example and not limited to succinic acid, ascorbic acid, glycolic acid, benzoic acid, sorbic acid, octanoic acid, adipic acid.

The antibacterial composition of the present invention may preferably comprise one or more organic acids and/or their salts or esters selected from lactic acid, acetic acid, citric acid, malic acid, fumaric acid, tartaric acid, gluconic acid, propionic acid, caproic acid and phytic acid as these acids further enhance the antibacterial activity while not negatively affecting the quality of the products in which they are applied in terms of for example taste, texture, color and odor.

In a further preferred embodiment, the antibacterial composition of the present invention further comprises a glycerol-based fatty acid ester. Said glycerol fatty acid ester, also referred to as glyceride, may comprise a monoester, a di-ester or a tri-ester of glycerol or mixtures hereof. Said glycerides have been observed to further increase the antibacterial effect against gram-negative bacteria.

The present invention further relates to the use of the antibacterial composition of the present invention as antibacterial agent against gram-negative bacteria. It is found that the antibacterial compositions of the present invention in particular show a very high (synergistic) activity against *Escherichia coli Salmonella* spp, *Pseudomonas* spp and *Campylobacter* spp. Accordingly, the fatty acid ester of fatty acid and hydroxycarboxylic acid (and/or a salt of ester hereof) may be effectively used as antibacterial agent in a composition according to the present invention (i,e, comprising polylysine, protamine, salts hereof and any combination hereof) against gram-negative bacteria and in particular against *Escherichia coli, Salmonella* spp, *Pseudomonas* spp and *Campylobacter* spp.

The various described antibacterial compositions of the present invention are applicable in a great variety of products and applications, ranging from for example products of low and high pH-values, highly concentrated and diluted products, products usable in the technical field (e.g. in detergents for industrial or house-hold use), in the pharmaceutical field (e.g. for cleaning/disinfection of equipment or in the preparation of pharmaceutical compositions or their packaging), in personal care (e.g. in manufacture of cosmetics, shampoos, creams and lotions), in the feed industry (e.g. for cleaning of equipment, in the manufacture, storage, handling and preparation of animal feed and drink products) and in the food and drink industry.

The present invention is accordingly related to the use of the antibacterial composition of the present invention for reduction or prevention of the presence, growth or activity of gram-negative bacteria, and in particular bacteria from the family of *Escherichia coli, Salmonella, Pseudomonas* or *Campylobacter*, in or for the manufacture, handling, storage and preparation of a food or drink product, a feed or drink product for animals, a cosmetic or personal care product, a cleaning product or a detergent.

Further, the present invention is directed to the use of fatty acid ester of fatty acid and hydroxycarboxylic acid (and/or a salt of ester hereof), in particular mono- and/or di-lactylate esters of octanoic acid (C8), or decanoic acid (C10), or dodecanoic acid (C12) or tetradecanoic acid (C14), or palmitic acid (C16), or oleic acid (C18:1) and the sodium, potassium and calcium salts hereof, as antibacterial agent, in particular against gram-negative bacteria, in a composition comprising polylysine, protamine and/or any salt or combination hereof.

The antibacterial composition of the present invention is especially very suited for reducing and/or preventing the presence, the growth and/or activity of any gram-negative bacteria cells in the manufacture, handling, application, storage and preparation of food and drink products.

It is very suitable for application in food and drink products such as beverages (e.g. carbonated soft drinks, fruit/vegetable-based juices), high protein-containing products such as meat and fish products, dressings and toppings, ready-to-eat and ready-to-drink products, refrigerated and high temperature-treated products.

When applied in the food or drink product, the fatty acid ester of the present invention such as e.g. a lactylate will normally be present in said product in an amount of up to 1% by weight of the product, preferably from 0.0001% to 1%, or even from 0.0001% to 0.1% and most preferably from 0.0001% to 0.01%.

Polylysine and/or protamine may be present in a food or drink product in an amount of up to 1% by weight of the product, preferably from 0.0001% to 1% or even from 0.0001% to 0.1%, more preferably from 0.0001% to 0.01% and most preferably from 0.0001% to 0.001%.

EDTA, organophosphates and polyphosphates will normally be present in a food or drink product in an amount of up to 1% by weight of the product, preferably from 0.0001% to 1%.

Organic acids such as for example lactic acid, fumaric acid, succinic acid, tartaric acid, ascorbic acid, glycolic acid, benzoic acid, citric acid, acetic acid, propionic acid, octanoic acid, malic acid and adipic acid may be present in a food or drink product in an amount of up to 10% by weight of the product, preferably from 0.0001% to 10%, preferably from 0.0001% to 5%.

In above-mentioned applications, the antibacterial composition of the present invention is present as ingredient in the final food or drink product.

The antibacterial composition may be present on the surface of said products or inside the products. The present invention is related to a method for reducing or preventing the presence, growth or activity of gram-negative bacteria in a food or drink product wherein said method comprises contacting said food or drink product during one or more of the various stages in the food processing process including the stages of the manufacture, the handling, the storage and/or the preparation of said food or drink product with the antibacterial compositions of the present invention. It may be applied not only in the final product stage but also during or in for example the disinfection of carcasses in the manufacture of meat products or in the washing step applied for fruit and vegetables. The antibacterial composition may be applied or introduced by various means such as for example as a spray, a rinse or a wash solution or as solution wherein the various food products are dipped. The antibacterial composition of the present invention may also be introduced by injection into the food and/or drink product. Further, the antibacterial composition may be used to treat containers with prior to, simultaneously with or subsequently after packaging the food and drink products.

Dependent on the type of application and on whether the antibacterial composition of the present invention is used as active ingredient in the final product or as component of for example a wash solution or spray solution, the components of the antibacterial composition will vary in concentration and in internal ratio as will be obvious to the person skilled in the art.

The antibacterial composition may be available in solid or liquid form. If the antibacterial composition is in liquid form, it generally is in the form of an aqueous composition, which may be a solution or a dispersion. Such aqueous antibacterial composition according to the present invention generally comprises, based on total weight of the solution, from 0.0001 wt % to up to 40 wt %, more preferably from 0.1 wt % to 35 wt %, and most preferably from 1 to 25 wt % of an antibacterial agent of the present invention such as e.g. polylysine and from 0.0001 wt % up to 45 wt. %, more preferably from 1 to 40 wt %, and most preferably from 5 to 35 wt % of fatty acid ester according to the present invention such as e.g. lactylate. The antibacterial composition may further comprise a glyceride in an amount of 0 to 45 wt % and more preferably from 0 to 35 wt % and further an organic acid in the range of 0 to 45 wt % and more preferably from 0 to 30 wt %.

The components of the antibacterial composition according to the present invention may be introduced in the liquid antibacterial composition by means of carriers. The person skilled in the art knows what type of carriers can be used. Among various well-known carriers, it was found that polyethylene glycol and/or lactate function very well as carrier. The carrier may be present in concentrations of about 50 to 98 wt %. Further, various emulsifiers known to the person skilled in the art may be added. Preferably emulsifiers such as polysorbates (e.g. polysorbate 60 or 80) and lecithine are applied in concentrations of for example 0.1 to 25%, more preferably 1-10% and most preferably 2 to 4% based on 100% fatty acid derivative, such as glyceride and/or lactylate.

If the antibacterial composition is in solid form, it will generally be in the form of a powder comprising particles of the relevant components. The antibacterial composition in solid form generally comprises, based on total weight of the powder, from 0.0001 wt % to up to 40 wt %, more preferably from 0.1 wt % to 35 wt %, and most preferably from 1 to 25 wt % of an antibacterial agent of the present invention such as e.g. polylysine and from 0.0001 wt % up to 45 wt. %, more preferably from 1 to 40 wt %, and most preferably from 5 to 35 wt % of fatty acid ester derivative according to the present invention such as e.g. lactylate.

Use may be made of carriers. Very suitable carriers are silica and/or maltodextrine, which are present in concentrations up to 50 to 98 wt %.

The antibacterial composition may further comprise a glyceride in an amount of 0 to 45 wt % and more preferably from 0 to 35 wt % and further an organic acid in the range of 0 to 45 wt % and more preferably from 0 to 30 wt %.

The following non-limiting examples further illustrate the invention.

EXAMPLE 1

The following cultures were used in a study: *Escherichia coli* serotype O157:H7 (ATCC 700728), *Salmonella typhimurium* (ATCC 13311) and *Salmonella entiritidis* (ATCC 13076). All cultures were transferred daily in screw-capped tubes containing 10 ml brain heart infusion broth. Cultures were incubated at 30° C. without agitation. Brain heart infusion broth was prepared with increasing amounts of lactylate and polylysine. The concentration range for the caprylic (C8) lactylate was as from 0 to 0.45% in 10 0.05% steps, for the capric (C10) lactylate was as from 0 to 0.09% in 10 0.01% steps, for the lauric (C12) lactylate was as from 0 to 0.009% in 10 0.001% steps and for the tetradecanoic (C14) lactylate was as from 0 to 0.009% in 10 0.001% steps. Lactylates were combined with polylysine. The concentration range for the polylysine was as from 0 to 0.0675% in 10 0.0075% steps. This resulted in 100 different media. The pH of the media was adjusted to 6.1-6.2 with 1 N HCl or 1 N NaOH. Media were prepared in 10 ml quantities and sterilized by filtration. 300 μl of each medium was transferred to a panel of a sterile Bioscreen® honeycomb 100 well plate. Well plates were inoculated with 5 μl of a culture that was grown overnight in brain heart infusion broth using a sterile 5 μl repeating dispenser. Growth rates were determined with a Bioscreen® C that kinetically measures the development of turbidity by vertical photometry. The plates were incubated for 16-24 hours at 37° C., the optical density of the cultures was measured every 30 minutes at 420-580 nm using a wide band filter. The Bioscreen® measures at set time intervals the optical density of the cultures. From these data the Bioscreen® calculates maximum specific growth rates. The purpose of further data processing is to ascertain whether two amino acids act independently of each other or whether they stimulate each other in their inhibitory action (synergy) or cancel out each other inhibitory effect (antagonism). When a certain compound has no effect on an organism the specific growth rate of this organism (μ) can be expressed as a function (f) of the growth limiting substrate concentration (s) by for example the Monod equation, which reads: $\mu=\mu_{max}\cdot s/(K_s+s)$, where $\mu_{max}$ represents the maximum specific growth rate, s the standing concentration of the growth limiting substrate in the medium and $K_s$ the substrate concentration where $\mu=0.5\mu_{max}$. However, when the presence of an inhibitor P affects cell growth the function f for μ must be modified i.e. $\mu=f(s,p)$, where p represents the concentration of inhibitor P. Numerous studies of growth inhibition kinetics of bacteria have shown that many inhibitors behave as non-competitive inhibitors. This implies that only the maximum specific growth rate ($\mu_{max}$) value and not the affinity ($K_s$) is affected. Therefore the specific growth rate in the presence of inhibitor can be written as: $\mu=\mu_i\cdot s/(K_s+s)$, where $\mu_i$ is the maximal specific growth rate in the presence of a inhibitor P. The relationship between $\mu_i$ and $\mu_{max}$ and the concentration of the inhibitor P was describes using the Logistic Dose Response equation, which reads: $\mu_i/\mu_{max}=1/(1+(p/p_{0.5})^b)$ (Jungbauer, A. (2001). The logistic dose response function: a robust fitting function for transition phenomena in life sciences. J. Clinical Ligand Assay 24: 270-274). In this equation p represents the concentration of inhibitor P and $p_{0.5}$ the concentration of P where $\mu_i=0.5\mu_{max}$; $\mu_{max}$ is the maximum specific growth rate that is the specific growth rate in the absence of inhibitor P, b is a dimensionless quantity, which determines the relationship between $\mu_i$ and p. Combining the Monod and Logistic Dose Response equation it can be written as: $\mu=\mu_{max}(s/K_s+s)/(1+(p/p_{0.5})^b)$. In batch culture where s is usually many times higher than $K_s$ this equation reduces to $\mu=\mu_{max}/(1+(p/p_{0.5})^b)$. When comparing different organisms grown under the same conditions, or the same organism grown under different conditions, it is more meaningful to use relative growth rate, rather than absolute growth rates as standards of comparison. Relative growth rate (O) is the ratio of growth rate (μ) to maximum growth rate ($\mu_{max}$) i.e. $O=\mu/\mu_{max}$. It can be seen that while μ and $\mu_{max}$ have the dimensions of (time)$^{-1}$, their ratio O is dimensionless, i.e. a pure number. Similarly we can define the relative inhibitor concentration ϵ as $p/p_{0.5}$. The reduced Monod and Logistic Dose Response equation can now be written as: $O=1/(1+\epsilon^b)$. For two inhibitors X and Y e.g. the following two expressions for O can be defined: $O_x=1/(1+\epsilon^{b1})$ and $O_y=1/(1+\epsilon^{b2})$. $O_x$ and $O_y$ can be experimentally evaluated by examining the inhibitory effects of either X or Y on the growth rate of the target organism. Knowing the evaluated functions for $O_x$ and $O_y$ the theoretical independent effect is defined as: $O_x\cdot O_y$. The experimentally observed effect of combinations of X and Y on the relative growth rate is defined as $O_{xy}$. The hypothesis that X and Y act independently of each other on a certain organism mathematically translates to $O_{xy}/O_x\cdot O_y=1$. Rejection of this hypothesis implies that the combined effect of X and Y is not an independent effect but either synergistic or antagonistic. In case the inhibitors X and Y act synergistically upon the target organism $O_{xy}/O_x\cdot O_y<1$ (but >0). In those cases that the combined effect of inhibitors X and Y is antagonistic $O_{xy}/O_x\cdot O_y>1$.

Figure 1:
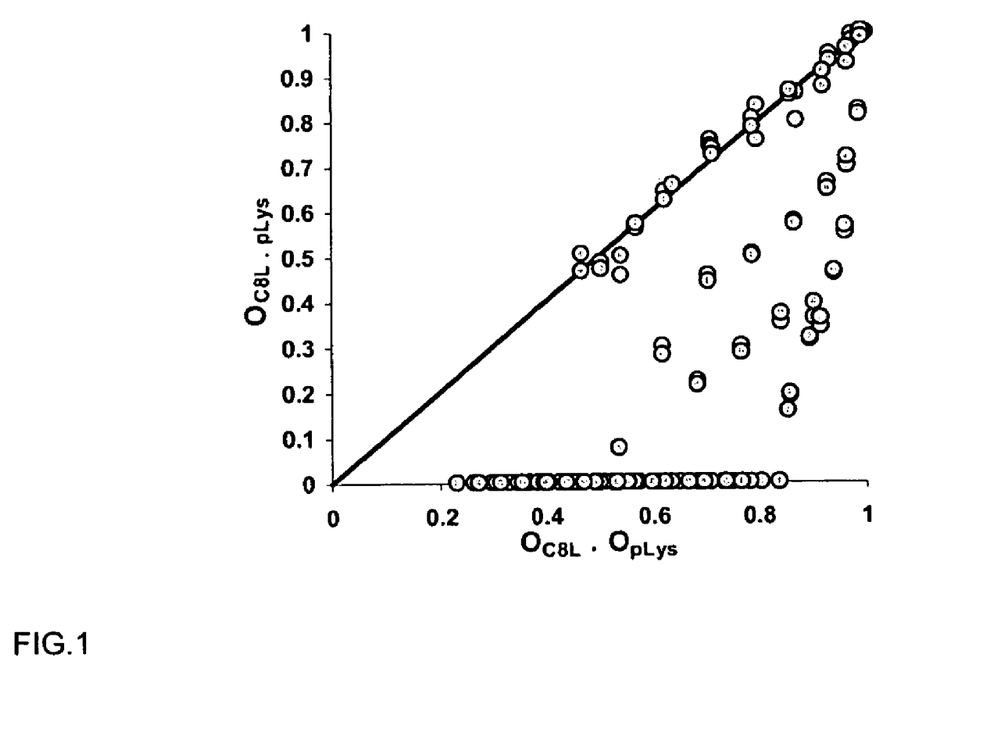
FIG. 1 represents a plot of experimentally observed relative growth rate of *Salmonella typhimurium* in the presence of mixtures of a C8-lactylate and polylysine ($O_{C8L\cdot pLys}$) versus predicted relative growth rate in the presence of mixtures of C8-lactylate and polylysine ($O_{C8L} \cdot O_{pLys}$).
Figure 2:
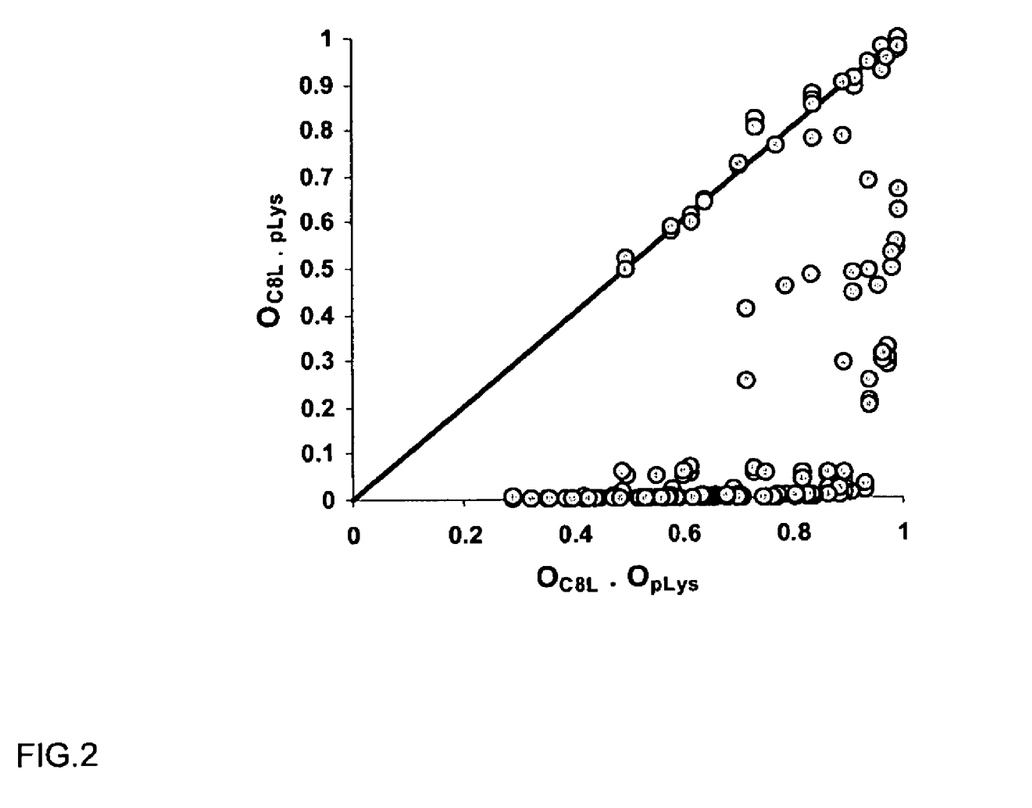
FIG. 2 represents a plot of experimentally observed relative growth rate of *Salmonella entiritidis* in the presence of mixtures of a C8-lactylate and polylysine ($O_{C8L \cdot pLys}$) versus predicted relative growth rate in the presence of mixtures of C8-lactylate and polylysine ($O_{C8L} \cdot O_{pLys}$).
Figure 3:
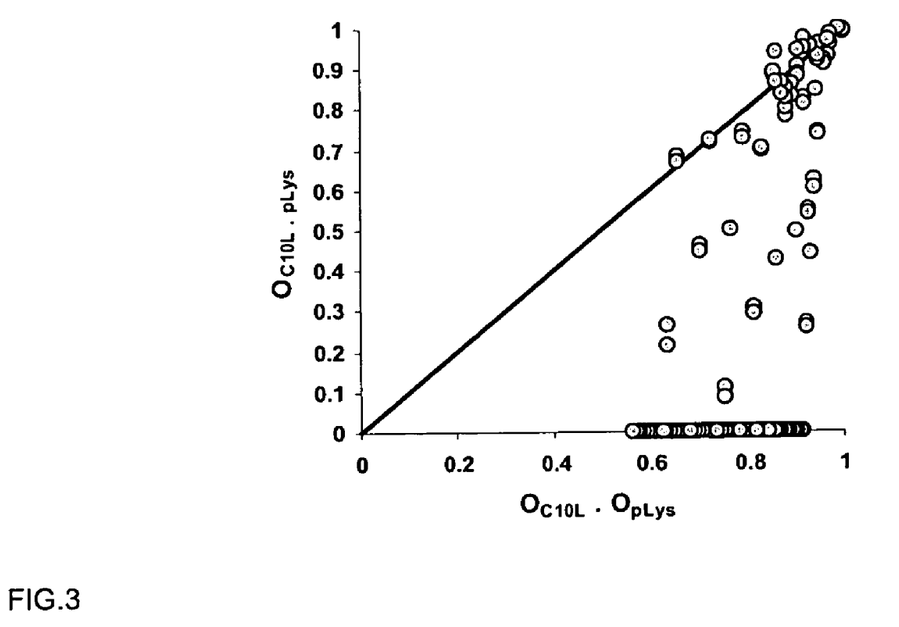
FIG. 3 represents a plot of experimentally observed relative growth rate of *Salmonella typhimurium* in the presence of mixtures of a C10-lactylate and polylysine ($O_{C10L \cdot pLys}$) versus predicted relative growth rate in the presence of mixtures of C10-lactylate and polylysine ($O_{C10L} \cdot O_{pLys}$).
Figure 4:
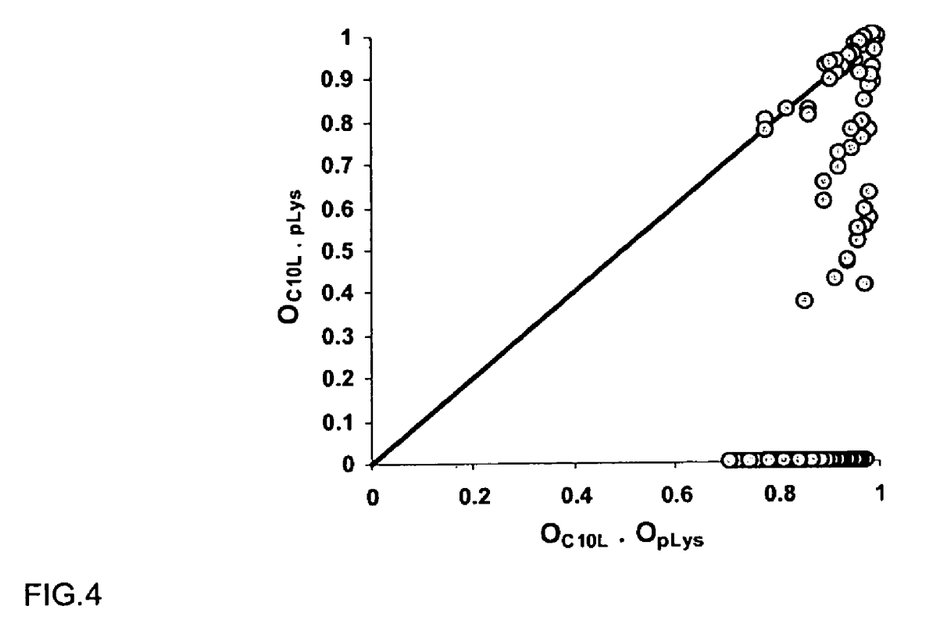
FIG. 4 represents a plot of experimentally observed relative growth rate of *Salmonella entiritidis* in the presence of mixtures of a C10-lactylate and polylysine ($O_{C10L \cdot pLys}$) versus predicted relative growth rate in the presence of mixtures of C10-lactylate and polylysine ($O_{C10L} \cdot O_{pLys}$).
Figure 5:
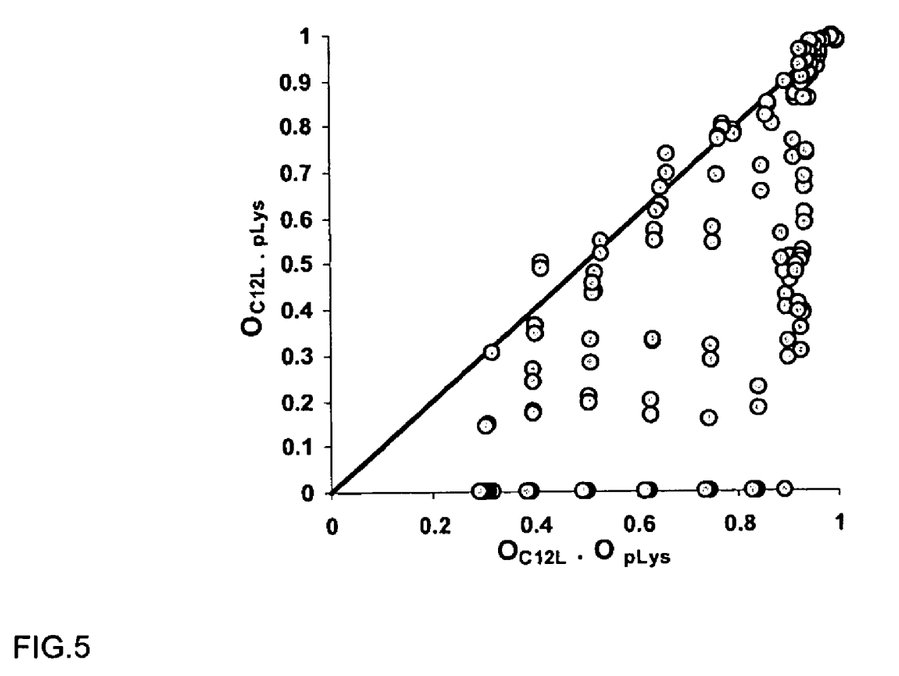
FIG. 5 represents a plot of experimentally observed relative growth rate of *Salmonella typhimurium* in the presence of mixtures of a C12-lactylate and polylysine ($O_{C12L \cdot pLys}$) versus predicted relative growth rate in the presence of mixtures of C12-lactylate and polylysine ($O_{C12L} \cdot O_{pLys}$).
Figure 6:
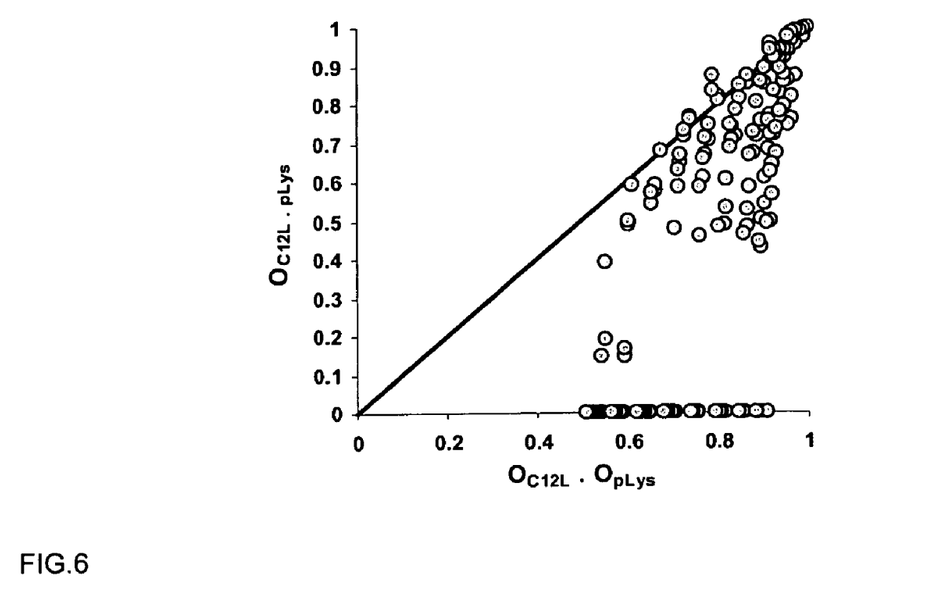
FIG. 6 represents a plot of experimentally observed relative growth rate of *Salmonella entiritidis* in the presence of mixtures of a C12-lactylate and polylysine ($O_{C12L \cdot pLys}$) versus predicted relative growth rate in the presence of mixtures of C12-lactylate and polylysine ($O_{C12L} \cdot O_{pLys}$).
Figure 7:
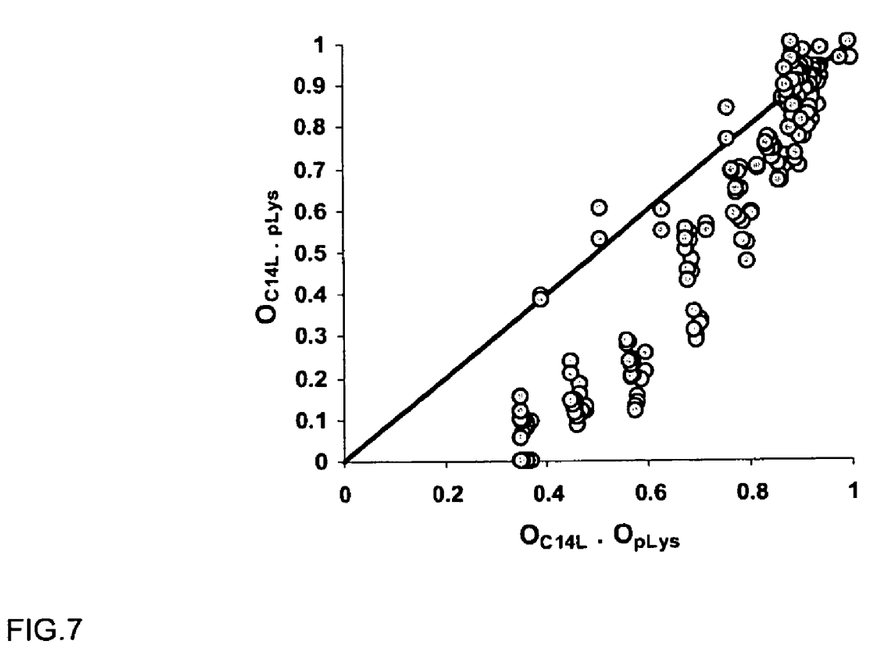
FIG. 7 represents a plot of experimentally observed relative growth rate of *Salmonella typhimurium* in the presence of mixtures of a C14-lactylate and polylysine ($O_{C14L \cdot pLys}$) versus predicted relative growth rate in the presence of mixtures of C14-lactylate and polylysine ($O_{C14L} \cdot O_{pLys}$).
Figure 8:
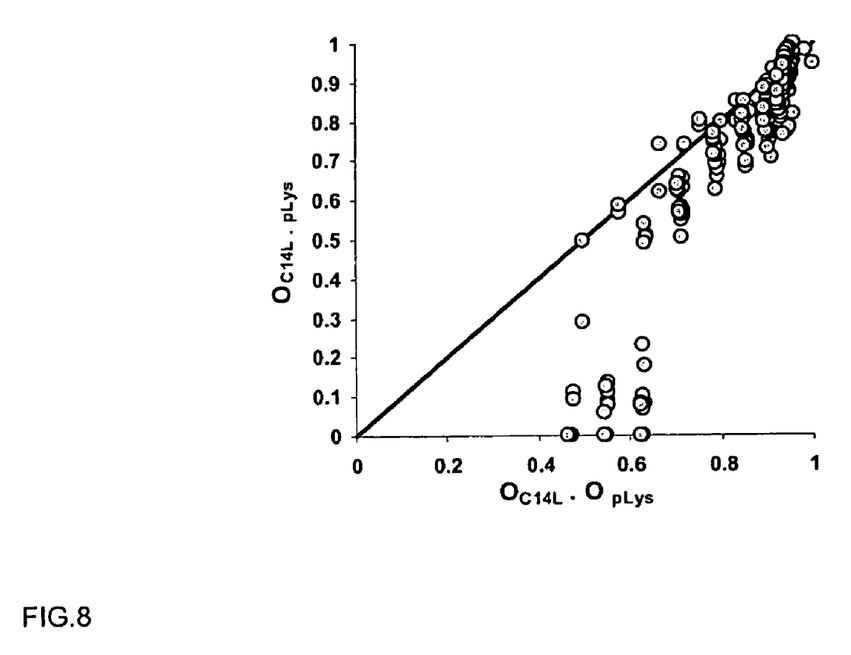
FIG. 8 represents a plot of experimentally observed relative growth rate of *Salmonella entiritidis* in the presence of mixtures of a C12-lactylate and polylysine ($O_{C12L \cdot pLys}$) versus predicted relative growth rate in the presence of mixtures of C12-lactylate and polylysine ($O_{C12L} \cdot O_{pLys}$).

Synergy, independent effect, and antagonism can be visualized in a plot of $O_{xy}$ versus $O_x\cdot O_y$. This is exemplified in FIG. 1-8, wherein different plots are given of $O_{CxL\cdot pLys}$ (experimentally observed relative growth rate in the presence of mixtures of a lactylate and polylysine) versus $O_{CxL}\cdot O_{pLys}$ (predicted relative growth rate in the presence of mixtures of a lactylate and polylysine) for *Salmonella typhimurium* (ATCC 13311) and *Salmonella entiritidis* (ATCC 13076) showing the synergy in inhibition between lactylates and polylysine. The solid line in these graphs represents the line where the experimentally observed relative growth rate ($O_{CxL\cdot pLys}$) equals the predicted relative growth rate ($O_{CxL}\cdot O_{pLys}$) and where the lactylate and polylysine act as independent inhibitors.

FIGS. 1-8 demonstrate that polylysine and lactylates in the various combinations tested act synergistically upon the target organism as $O_{xy}/O_x \cdot O_y < 1$ and $>0$ (represented by the dots below the solid line).

Further examples of synergy are given in Table 1 such as for example the synergy between 0.0225% (w/w) polylysine and 0.45% (w/w) C8-lactylate or 0.0225% (w/w) polylysine and 0.09% (w/w) C10-lactylate or 0.0225% (w/w) polylysine and 0.009% C12-lactylate or 0.0225% (w/w) polylysine and 0.009% C14-lactylate.

As can be observed in the Table, the relative growth rate of *Escherichia coli* (ATCC 8739), *Escherichia coli* serotype O157:H7 (ATCC 700728), *Salmonella typhimurium* (ATCC 13311) or *Salmonella entiritidis* (ATCC 13076) in a broth containing 0.0225% (w/w) polylysine and 0.45% (w/w) C8-lactylate or 0.0225% (w/w) polylysine and 0.09% (w/w) C10-lactylate or 0.0225% (w/w) polylysine and 0.009% C12-lactylate or 0.0225% (w/w) polylysine and 0.009% C14-lactylate is lower than can be expected on the basis of the relative growth rate of these organisms in media containing either polylysine or one of the lactylate esters.

TABLE 1

Examples of synergy

| | Observed Relative Growth Rate | | |
|---|---|---|---|
| Compound Concentration (w/w) | C8-lactylate 0.45% | polylysine 0.0225% | C8-lactylate plus polylysine 0.45%/0.0225% |
| *Escherichia coli* ATCC 8739 | 0.5625 | 0.68 | 0.0000 |
| *E. coli* O157:H7 ATCC 700728 | 0.657 | 0.838 | 0.0403 |
| *Salmonella typhimurium* ATCC 13311 | 0.47625 | 0.943 | 0.0000 |
| *S. enteritidis* ATCC 13076 | 0.58 | 0.9645 | 0.0000 |

| | Observed Relative Growth Rate | | |
|---|---|---|---|
| Compound Concentration (w/w) | C10-lactylate 0.09% | polylysine 0.0225% | C10-lactylate plus polylysine 0.09%/0.0225% |
| *Escherichia coli* ATCC 8739 | 0.721 | 0.4935 | 0.0171 |
| *E. coli* O157:H7 ATCC 700728 | 0.766 | 0.489 | 0.0000 |
| *Salmonella typhimurium* ATCC 13311 | 0.904 | 0.9725 | 0.0000 |
| *S. enteritidis* ATCC 13076 | 0.912 | 0.971 | 0.0000 |

| | Observed Relative Growth Rate | | |
|---|---|---|---|
| Compound Concentration (w/) | C12-lactylate 0.009% | polylysine 0.0225% | C12-lactylate plus polylysine 0.009%/0.0225% |
| *Escherichia coli* ATCC 8739 | 0.7820 | 0.7370 | 0.0027 |
| *E. coli* O157:H7 ATCC 700728 | 0.9230 | 0.6070 | 0.0000 |
| *Salmonella typhimurium* ATCC 13311 | 0.9525 | 0.9520 | 0.2663 |
| *S. enteritidis* ATCC 13076 | 0.9475 | 0.9035 | 0.0000 |

| | Observed Relative Growth Rate | | |
|---|---|---|---|
| Compound Concentration (w/w) | C14-lactylate 0.009% | polylysine 0.0225% | C14-lactylate plus polylysine 0.009%/0.0225% |
| *Escherichia coli* ATCC 8739 | 0.4750 | 0.4395 | 0.0000 |
| *E. coli* O157:H7 ATCC 700728 | 0.8850 | 0.2800 | 0.0000 |

EXAMPLE 2

Antimicrobial Effect in Contaminated Chicken Filet and Milk

Materials and Methods

Culture and Culturing Conditions

*Salmonella Typhimurium* ATCC 13311 and *Escherichia coli* O157:H7 ATCC 700728 were grown in sterile screw capped tubes containing Brain heart infusion broth for 18-24 hours at 30° C.

Preparation of Chicken Filets

Chicken filets (150-200 g) were trimmed, vacuum packaged and stored at 4-7° C. Filets were subsequently sterilized by gamma-irradiation (average radiation dose: 12 kiloGray).

Inoculation of Chicken Filets with *Salmonella Typhimurium*.

1 ml of an overnight culture of *Salmonella Typhimurium* in brain heart infusion both was diluted 1000 times with sterile 0.8% (w/v) NaCl and 0.1% (w/v) peptone. 0.5 ml of this diluted culture was transferred to one side of the filet. The inoculum was distributed by gently rubbing the entire surface of the filet. This was repeated for the other side of the filet. Inoculation was carried out at 6° C. Inoculated filets were rested for 60-120 min at 6° C. to allow attachment of the cells.

Decontamination of Chicken Filets

Chicken filets were briefly dipped and completely submersed in 1 l of a solution containing the appropriate formulation and then transferred to 400 ml Bagfilter® lateral filter bags (Interscience, St Nom, France) containing 5 ml of the appropriate formulation. Bags were vacuum-sealed and incubated at 12° C. for up to 7 days until further analysis. Time zero samples were plated within 30 min after dipping.

Microbial Analysis of Chicken Filets.

Surviving *Salmonella Typhimurium* on chicken filets were counted as follows: a sealed bag was opened and to this was added 2 times the net weight sterile dilution fluid (8.5% (w/v) NaCl and 0.1% (w/v) bacteriological peptone). Duplicate filets were homogenized for 1 min. in a Bagmixer® 400 paddle labblender (Interscience, St Nom, France). 50 µl of the homogenates or dilutions thereof were plated on duplicate *Salmonella* chromogenic agar plates (CM1007) with cefsulodin, novobiocin supplement (SR0194) (Oxoid, Basingstoke, United Kingdom) using an Eddyjet type 1.23 spiral plater (IUL Instruments, Barcelona, Spain). Plates were incubated for 24-48 hours at 30° C. and then counted. *Salmonella* numbers were expressed as $\log_{10}$ colony forming units per ml homogenate.

Inoculation of Milk Treated with Antimicrobial Formulations

Sterile low fat milk was purchased from a local supermarket and 100 ml quantities were transferred to a series of sterile screw topped bottles. ε-Polylysine, The sodium salt of octanoyllactylate (C8-lactylate) and decanoyllactylate (C10 lactylate) were added to a concentration as shown in Table 2. The different milk preparations were inoculated with an overnight culture of *Escherichia coli* O157:H7. The starting cell density was $\log_{10}$ 2.5-3.0.

Microbial Analysis of Milk Cultures

Surviving *Escherichia coli* O157:H7 were counted as follows: duplicate 50 µl samples of milk cultures or dilutions thereof were plated on duplicate Violet Red Bile Glucose (VRBG) agar plates (CM0485 Oxoid, Basingstoke, United Kingdom) using an Eddyjet type 1.23 spiral plater (IUL Instruments, Barcelona, Spain). Plates were incubated for 24-48 hours at 30° C. and then counted. *Escherichia coli* numbers were expressed as $\log_{10}$ colony forming units per ml homogenate.

Preparation of Antimicrobial Formulations

The compositions of the formulations that were studied are shown in Table 2. ε-Polylysine and lactylates were dissolved in demineralised water and sterilized for 20 min at 120° C.

TABLE 2

Composition of antimicrobial formulations

| Formulation | Blanc | a | b |
|---|---|---|---|
| ε-polylysine | | 0.1% (w/v) | 0.1% (w/v) |
| C8-Lactylate | | 0.2% (w/v) | |
| C10-lactylate | | | 0.05% (w/v) |
| NaCl | 0.8% (w/v) | 0.8% (w/v) | 0.8% (w/v) |

Chemicals

ε-Polylysine was purchased from Chisso America Inc (New York, USA). The sodium salt of octanoyllactylate (C8-lactylate) and decanoyllactylate (C10 lactylate) were purchased from Caravan Ingredients (Lenexa, Kans., USA).

Results Decontamination of Chicken Filets

Exposure of *Salmonella Typhimurium* ATCC 13311 present on chicken filets to combinations of ε-polylysine with lactic acid esters of medium chain fatty acid esters resulted in an almost immediate reduction of the number of viable cells by approximately 90% (Table 3). After one day at 12° C. the reduction in numbers is more than a 4 $\log_{10}$. The suppression of growth by the tested combinations is not permanent; after 4 days the numbers have increased although after 7 days after incubation the difference between the formulations and the blanc formulation is never less than 2 $\log_{10}$ and the composition of the present invention thus still exerts antimicrobial activity.

TABLE 3

Effect of combinations of ε-polylysine (ε-PL) with lactic acid esters of medium chain fatty acid esters on *Salmonella Typhimurium* on chicken filets at 12° C.; expressed in $\log_{10}$ colony forming units (CFU)/ml

| | Formulation | | |
|---|---|---|---|
| Time (days) | Blanc | 0.1% (w/v) ε-PL + 0.2% (w/v) C8-Lactylate | 0.1% (w/v) ε-PL + 0.05% (w/v) C10-lactylate |
| 0 | 3.74 | 2.40 | 2.62 |
| 1 | 5.91 | 1.3 | 1 |
| 4 | 6.01 | 3.03 | 2.64 |
| 5 | 6.89 | 4.26 | 4.25 |
| 6 | 7.36 | 3.68 | 3.96 |
| 7 | 7.46 | 5.46 | 4.66 |

Individually the lactylates did not show any killing or growth suppressing effect in the absence of ε-polylysine as can be observed in Table 4. ε-Polylysine itself reduced the cell numbers although the effect was less than if it was combined with one of the fatty acid derivatives. This was particularly clear after one day of incubation. Whereas the reduction in numbers for the combinations ranged from 4 $\log_{10}$ to 5 $\log_{10}$ (Table 3) the reduction for ε-polylysine as single addition was only 2 $\log_{10}$ (Table 4). This suggests that there is a form of synergy in inhibition between ε-polylysine and the fatty acid derivatives. This is confirmed by in vitro studies in which the effects of these combinations were studied in broth (experiment 1).

TABLE 4

Individual effect of ε-polylysine and C8 and C10 lactic acid esters of medium chain fatty acid esters on *Salmonella Typhimurium* on chicken filets at 12° C.; expressed in $\log_{10}$ colony forming units (CFU)/ml

| | | Formulations | | |
|---|---|---|---|---|
| Time (days) | Blanc | 0.1% (w/v) ε-polylysine | 0.2% (w/v) C8-Lactylate | 0.05% (w/v) C10-lactylate |
| 0 | 3.8 | 3.04 | 3.85 | 3.75 |
| 1 | 4.05 | 2.04 | 4.1 | 3.95 |
| 2 | 4.82 | 2.15 | 4.29 | 4.45 |
| 5 | 7.2 | 4.04 | 6.27 | 6.87 |
| 6 | 7.6 | 4.26 | 7.35 | 6.83 |
| 7 | 7.68 | 5.35 | 7.42 | 7.52 |

Results Inhibition of *Escherichia coli* O157:H7 in Milk

Strong inhibition of growth by combinations of ε-polylysine with lactic acid esters of medium chain fatty acid esters was also observed for *Escherichia coli* O157:H7 growing in non fat milk (Table 5)

TABLE 5

Effect of combinations of ε-polylysine (ε-PL) with lactic acid esters of medium chain fatty acid esters on *Escherichia coli* O157:H7 in milk at 12° C.; expressed in $\log_{10}$ colony forming units (CFU)/ml (ND: No data)

| | | Formulations | |
|---|---|---|---|
| Time (days) | Blanc | 0.2% (w/v) ε-PL + 0.2% (w/v) C8-Lactylate | 0.1% (w/v) ε-PL + 0.05% (w/v) C10-lactylate |
| 0 | 2.85 | 3.0 | 2.9 |
| 1 | 3.48 | 1.7 | 1.95 |
| 2 | 6.12 | 1.9 | 3.37 |
| 3 | 7.42 | 2.75 | 4.24 |
| 6 | ND | 5.6 | 5.89 |

The invention claimed is:

1. An antibacterial composition comprising a combination of
   a, a lactylate, or a mixture of lactylates, represented by the following formula:

wherein RCO is an acyl radical of a fatty acid having 4 to 18 carbon atoms, Y is a cation selected from the group consisting of hydrogen, alkali metal, alkaline earth metal, zinc, iron, ammonium or substituted ammonium having one or more C1-C3 alkyl or hydroxy alkyl groups; n represents the value of the cation; m is an integer of from 1 to n, x is a number of from 1 to 6 and wherein x, m and n represent average numbers, and
   b. a compound selected from the group consisting of polylysine, a salt of polylysine, and a mixture thereof.

2. The antibacterial composition of claim 1, wherein x has a value of from 1 to 3 and the lactylate is selected from octanoyllactylate, decanoyllactylate, dodecanoyllactylate, tetradecanoyl-lactylate, oleic-lactylate, in their free form or as salt, and a mixture thereof.

3. The antibacterial composition of claim 1, wherein the polylysine is ε-polylysine.

4. The antibacterial composition of claim 1, further comprising one or more additives selected from the group consisting of a metal chelating agent, an organic acid or a salt or ester thereof, a glycerol-based fatty acid ester or a mixture thereof.

5. The antibacterial composition of claim 4, wherein the organic acid is selected from the group consisting of lactic acid, acetic acid, citric acid, malic acid, fumaric acid, tartaric acid, gluconic acid, propionic acid, caproic acid and phytic acid.

6. The antibacterial composition of claim 4, wherein the fatty acid ester of glycerol is a mono- or di-ester of glycerol or a mixture thereof.

7. The antibacterial composition of claim 1, wherein the composition is a liquid or a solid and wherein the composition comprises from 0.0001 to 40 wt % of the compound, 0.0001 to 45 wt % of the lactylate, or the mixture of lactylates, 0 to 45 wt % of a glycerol-based fatty acid ester, 0 to 45 wt % of an organic acid or a salt or ester thereof, and 0 to 98 wt % of a carrier.

8. Method for reduction or prevention of the presence, growth or activity of gram-negative bacteria into, or on, a product or surface, the method comprising applying the antibacterial composition of claim 1 into the product, or on the surface.

9. The method according to claim 8, wherein the gram-negative bacteria is a bacterium from the family of *Escherichia coli, Salmonella, Pseudomonas* or *Campylobacter.*

10. A food or drink product, a cosmetic product, a personal-care product, a cleaning product, a detergent or a feed or drink product for animals comprising the antibacterial composition of claim 1.

* * * * *